United States Patent [19]
Inaba

[11] Patent Number: 4,983,041
[45] Date of Patent: Jan. 8, 1991

[54] SPECTROSCOPIC APPARATUS FOR EXTREMELY FAINT LIGHT

[76] Inventor: Fumio Inaba, 13-1, 1-chome, Yagiyamaminami, Sedai-shi, Miyagi-ken, Japan

[21] Appl. No.: 261,855

[22] Filed: Oct. 25, 1988

[30] Foreign Application Priority Data

Oct. 26, 1987 [JP] Japan .................................. 62-268316

[51] Int. Cl.$^5$ .............................................. G01J 3/45
[52] U.S. Cl. .................................................. 356/346
[58] Field of Search .................... 356/346; 250/213 R, 250/213 VT

[56] References Cited
U.S. PATENT DOCUMENTS

| | | | |
|---|---|---|---|
| 4,195,931 | 4/1980 | Hara | 356/346 |
| 4,523,846 | 6/1985 | Breckinridge et al. | 356/346 |
| 4,575,248 | 3/1986 | Horwitz et al. | 356/353 |
| 4,732,481 | 3/1988 | Matsui et al. | 356/346 |
| 4,750,834 | 6/1988 | Fateley | 356/346 |

Primary Examiner—Davis L. Willis
Assistant Examiner—Matthew W. Koren
Attorney, Agent, or Firm—Armstrong, Nikaido, Marmelstein, Kubovcik, & Murray

[57] ABSTRACT

The present invention relates to a photo-counting Fourier spectroscopic apparatus which enables spectroscopic detection of extremely fine emission light seen in a living-body specimen or the like as bioluminescence, chemiluminescence, and fluoroescence from a living-body specimen. A light from a specimen which emits an extremely faint light is guided to an interferometer. A two-dimensional photon counter is used as an interference fringe detector. The two-dimensional photo counting device counts the number of incident photons to form an image. The obtained image is subjected to Fourier analysis to thereby obtain spectral information about the incident light. A double beam interferometer, a triangular common path interferometer, a Michelson interferometer and other interferometers are used.

8 Claims, 4 Drawing Sheets

SPECTROSCOPIC APPARATUS FOR EXTREMELY FAINT LIGHT

BACKGROUND OF THE INVENTION

1. Field of the Invention

The present invention relates to a spectroscopic apparatus for extremely faint light emission, and more particularly, to a spectroscopic apparatus which enables spectroscopic detection of extremely faint light emission observed in the living-body specimen or the like as bioluminescence, chemiluminescence, and fluorescence from a living-body specimen.

2. Description of the Prior Art

For spectroscopic detection of extreme faint light emission such as bioluminescence, a spectroscopic method using color glass filters has been heretofore used. FIG. 7 is a block diagram for such an apparatus. Various specimens which generate extreme faint emission are received in a specimen cell or a container 21 which is controlled by a temperature regulator 22 to a predetermined temperature suitable for the measuring conditions. The emission from a light source is converged on a photoelectric surface of a photo multiplier (PM) using a tubular reflecting mirror of an ellipsoid of revolution 23. Color glass filters 25 used for spectrum analysis are arranged on a mechanically rotatable disk 26, and are successively inserted into and exchanged automatically in a measuring light path in front of the PM 24 by means of a filter drive and control device 27. The intensity of the transmitted light, after having been passed through a filter 25, is counted by the PM 24. The PM 24 used for measurement is cooled by a thermoelectric temperature control unit 28 in order to suppress heat noise pulses. Signals from the PM 24 are counted by an addition and subtraction counter 34 via a pulse amplifier 30 and a pulse height discriminator 31. A chopper 32 and a phase shifter 33 are provided to periodically intermittently feed incident light from the light source and effect digital lock-in detection. The results counted by the addition and subtraction counter 34 are recorded in a digital printer 35. Data processing, required for directly obtaining a spectral distribution, is carried out in a mini-computer 36. The results are displayed on an oscilloscope 37 and an X-Y recorder 38. In FIG. 7, reference numeral 29 designates a stabilized high voltage power source, and 39 designates a preset timer.

The spectroscopic method using color glass filters as described above is superior to a diffraction grating spectroscope in terms of brightness because light from the specimen is wholly detected. However, plural color glass filters are needed and therefore a disadvantage is that observation time becomes very long.

On the other hand, a spectroscope using a diffraction grating has a large F number which determines brightness. However, it is difficult to use the diffraction grating to detect a faint emission.

Recently, Fourier spectroscopy using a diode array is being used in various fields. This method is used where light for spectrum is relatively strong. It was impossible to use Fourier spectroscopy for spectrum analysis of an extremely faint emitted by a living specimen or the like due to the high noise of the diode.

Separate from the spectrum analysis of the extremely faint emission as described above, a two-dimensional photon counter which will be described later has been known as an apparatus for obtaining an image of a body emitting extremely faint light. However, this apparatus is merely used with a conventional spectroscope using a diffraction grating. No attempt has been made to use this apparatus with a bright spectroscope which can be used for spectroscopy of the extremely faint emission.

SUMMARY OF THE INVENTION

The present invention overcomes the disadvantages encountered in a conventional spectroscopy for an extremely faint emission. An object of the invention is to provide a spectroscopic apparatus which can detect the of an extremely faint emission such as a bioluminescence in a short period of time.

An extremely faint light spectroscopic apparatus according to the present invention is a spatial interferogram type Fourier spectroscopic apparatus comprising an optical system for dividing a light beam from a photon emitting source into two light beams, an optical system for focusing interference fringes of the divided two beams and a detector for detecting the focused interference fringes, in which a two-dimensional photon counter capable of detecting photon receiving positions is used as the detector.

An interferometer capable of using Fourier spectroscopic analysis of an extremely faint emission source may be obtained by the two-dimensional photon counter capable of detecting photon receiving positions used as the detector.

DETAILED DESCRIPTION OF THE PREFERRED EMBODIMENTS

Since an image of an object which merely produces an extremely faint emission is composed of an extremely small number of photons, the obtained image is a distribution of diffused luminous points corresponding to individual incident photons. As a technique to form an image of such an object producing an extremely faint emission, there is a technique in which the number of luminous points as described above, that is, the number of incident photons, is counted and formed into an image. For this purpose, a two-dimensional photon counter apparatus is used. One such counter is a device comprising a combination of a two-dimensional photon counting tube and a low persistence visicon (VIMS) as shown in FIG. 2 and a photon counting type image measuring device (PIAS) as shown in FIG. 3 are included.

Figure 2:
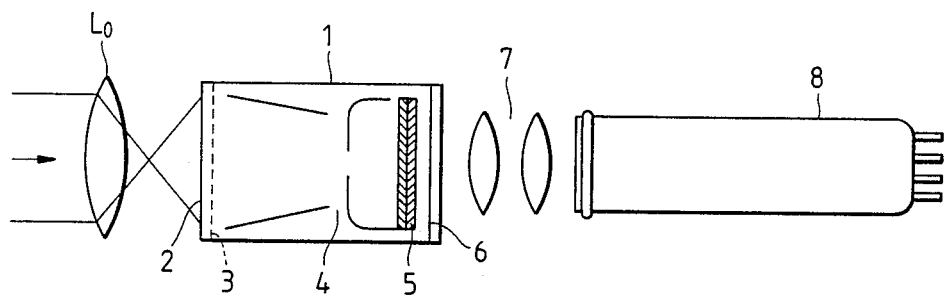
FIG. 2 is a sectional view of a combination of a two-dimensional photon counting tube used in this embodiment and a low persistence visicon.

In FIG. 2, a photon incident upon a photo-electric surface 2 of a two-dimensional photon counting tube 1 is converted into a photo-electron. The photo-electron is incident upon a two-stage connection microchannel plate (MCP) 5 via a mesh 3 and an electronic lens 4 and amplified and thence impinges upon an exit fluorescent surface 6 to form a luminous point. This luminous point is imaged on a photo-electric surface of a low persistence visicon 8 by means of a lens 7. Since a two-dimensional position of the luminous point, to which the photon corresponds, is obtained as a pulse signal by an output from the visicon 8, an image of an object of extremely faint emission is obtained by taking a distribution of the luminous points.

Figure 3:
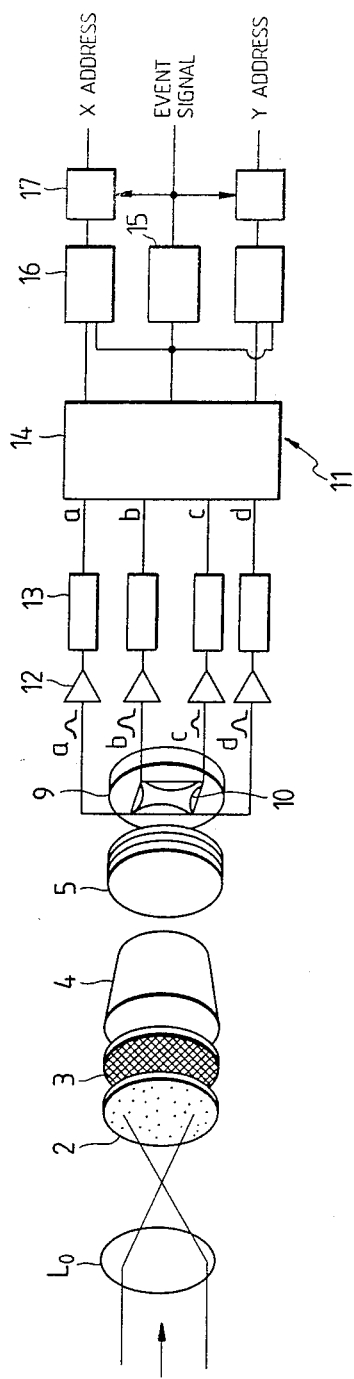
FIG. 3 is a sectional view of a photon counting type image measuring apparatus used in another embodiment.

In PIAS of FIG. 3, the structure from the photo-electric surface 2 to MCP 5 is similar to that of FIG. 2 (in the example of FIG. 3, MCP is of a three-stage connection), in which a group of electrons from MCP 5 is incident upon a silicon semiconductor position detector (PSD) 9 arranged therebehind, further amplified by an electron impact effect and is output as a pulse signal from PSD 9. PSD 9 is a charge distribution type position detector having four signal output electrodes 10 in the periphery thereof, in which the electric charges generated in the PSP 9 are distributed to these four electrodes 10 according to the position at which charges are generated via a resistant layer of the surface. As a result, signals corresponding to the centroidal position of a group of electrons incident upon the PSD 9, that is, the position of the luminous point, are obtained from the four electrodes 10. After pulse signals obtained from PSD 9 have been amplified by an amplifier 12, they are transmitted to a position calculator 11, where these pulse signals are integrated in integration circuits 13 to obtain an amount of electric charges from these electrodes 10. Then these signals are transmitted to an addition and subtraction circuit 14 and transmitted to a divider 16 through a window, gate 15 to convert them into position signals. The signals are AD-converted by an AD converter 17 to release them as output signals. The output signal is processed to obtain a distribution of luminous points whereby an image of an extremely faint emission object can be obtained. In FIGS. 2 and 3, reference character $L_o$ indicates an objective lens through which an incident photon (indicated by the arrow) is brought onto the photo-electric surface 2.

It is known that when an extremely faint emission light is incident upon a double slit forming an interference fringe, the light exhibits a dual character of a wave and a particle possessed by a photon. That is, in an initial stage, a diffusive distribution of luminous points appears in an interference surface but the whole shape is not yet indefinite. However, after a lapse of time, this distribution becomes dense to exhibit an image of an interference fringe. This image of interference fringe coincides with the result of a double beam interference calculated on the assumption that two beams having passed through a double slit, interfere with each other.

Figure 1:
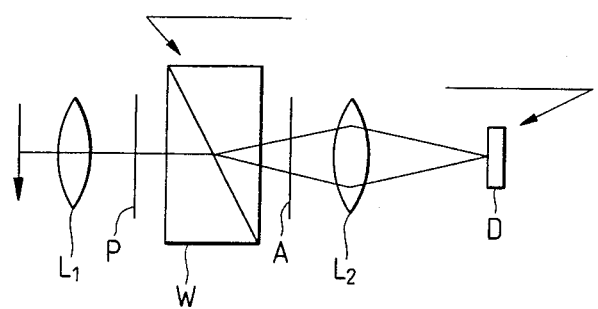
FIG. 1 shows a light path of a double beam interferometer used in an embodiment of an extremely faint spectroscopic apparatus according to the present invention.

One of the interferometers used in a Fourier spectroscopy of the type for producing a spatial interferogram is shown in FIG. 1. The photo-electric surface 2 of the device comprising a combination of a two-dimensional photon counting tube and a low persistence visicon in the aforesaid two-dimensional photon counter is arranged at a position of a detector D which is an interference surface of a double beam interferometer comprising, a polarizer P, a Wallaston prism W, an analyzer A and a focusing lens $L_2$ to obtain a luminous point distribution. Then, an interferogram capable of using Fourier spectroscopic analysis is possible.

The above-described Fourier spectroscopy, of the type which produces a spatial interferogram is that time series data obtained, by scanning a mirror in a normal Fourier spectroscopy which is spatially produced as an interferogram. The interferogram is subjected to analysis of spatial frequency distribution (Fourier transform) to obtain a spectral distribution of light. In FIG. 1, incident light from an extremely faint emission body via a collimation lens $L_1$ passes only in its predetermined polarized component through the polarizer P, which is divided into two polarized components perpendicular to each other by the Wallaston prism W to form an interferogram on the photo-electric surface 2 (FIG. 2), which is located at a position of the detector D, by a lens $L_2$ via the analyzer A. Since the interferogram is obtained by superimposing interference fringes (spacing of which depends upon the wavelength) formed by each wavelength component of light from an extremely faint emission source, it is subjected to spatial Fourier transform to analyze the spatial frequency distribution whereby spectral distribution of the light source can be obtained.

That is, the present invention provides a Fourier spectroscopic apparatus of a spatial interferogram type comprising an optical system for dividing a light from a photon emitting source into two beams. An optical system focuses interference fringes of the two beams and a detector detects the focused interference fringes. As the detector, a two-dimensional photon counting device capable of detecting photon receiving positions is used thereby enabling spectroscopic detection of bioluminescence, chemiluminescence, and fluorescent light from a living-body specimen, particularly an extremely faint emission seen in a living-body specimen or the like.

Figure 4:
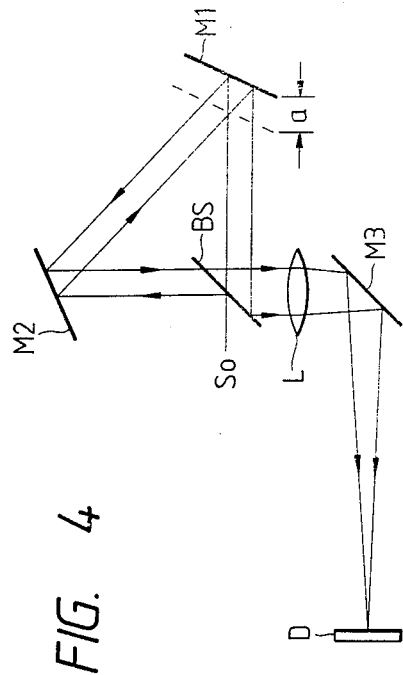
FIG. 4 shows a light path of a triangle common path interferometer used in another embodiment.
Figure 5:
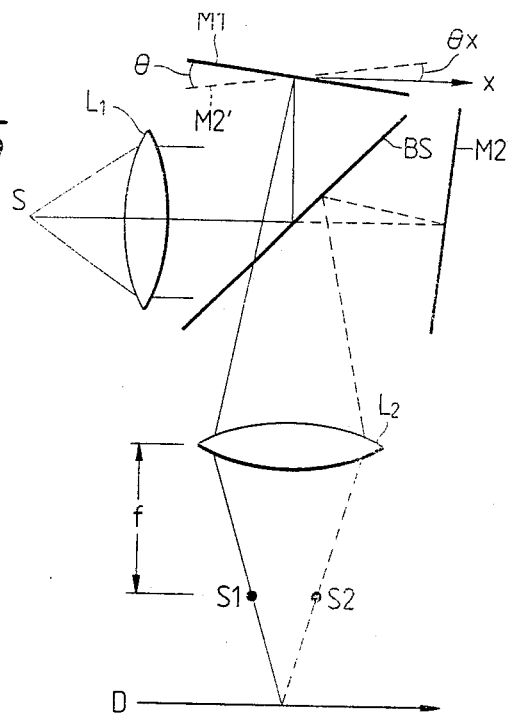
FIG. 5 shows a light path of a Michelson interferometer used in another embodiment.
Figure 6:
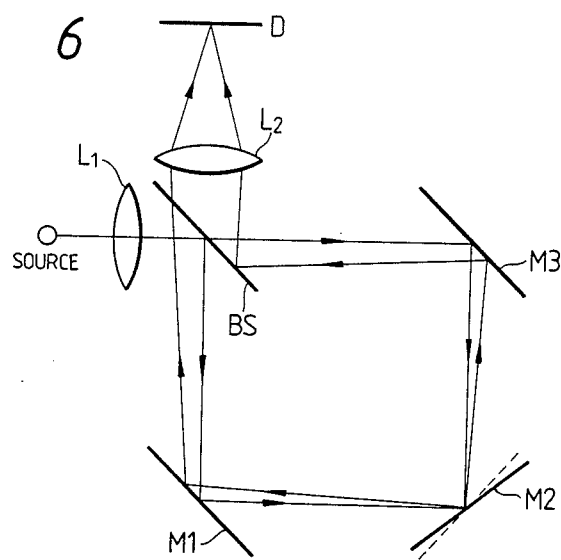
FIG. 6 shows a light path of a square common path interferometer used in another embodiment.
Figure 7:
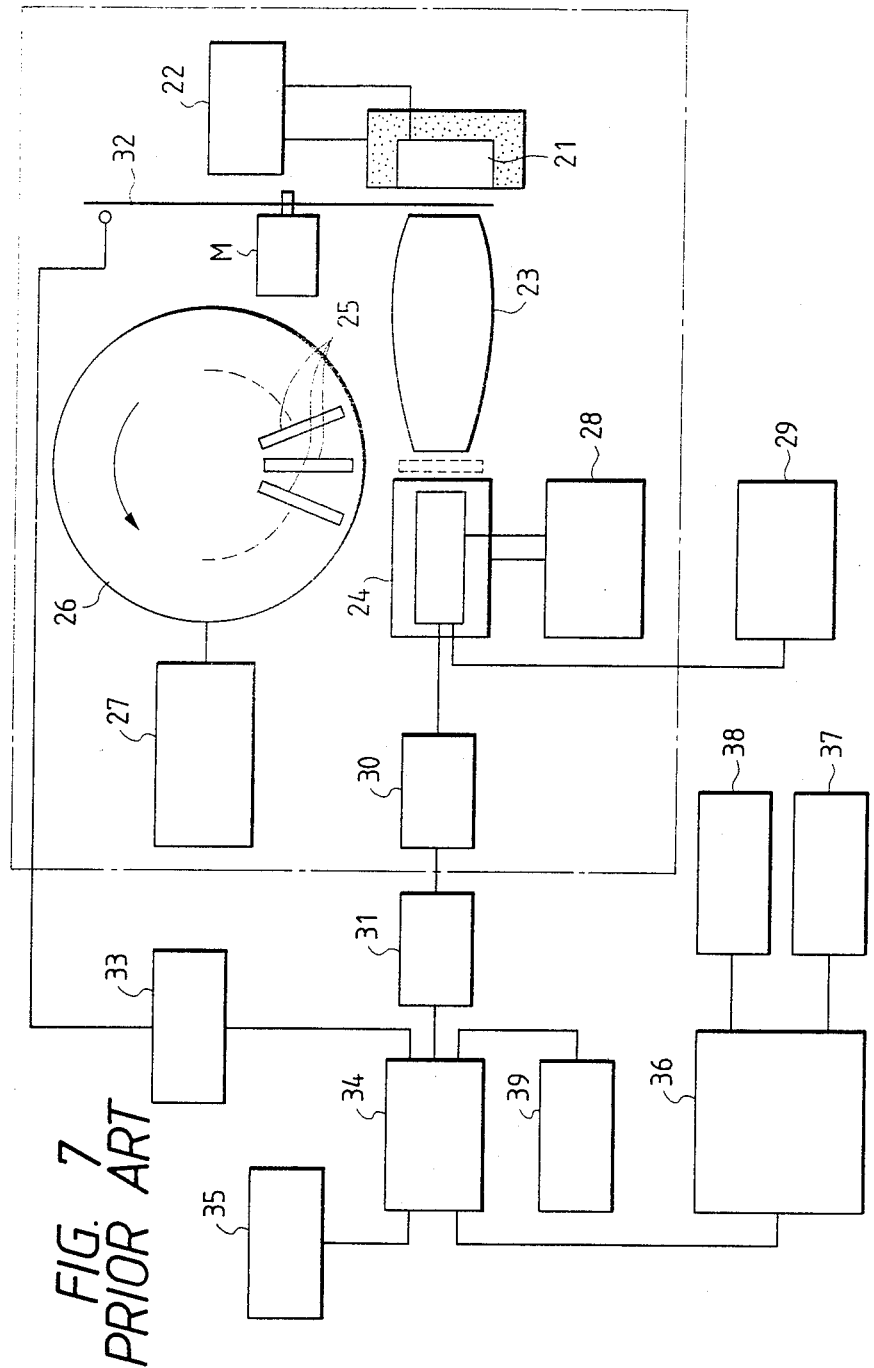
FIG. 7 is a block diagram of a conventional spectroscopic apparatus using color glass filters.

The optical system for focusing interference fringes of the two beams used in the extremely faint light spectroscopic apparatus includes, in addition to the interferometer as shown in FIG. 1, those shown in FIGS. 4 to 6, for example. The apparatus shown in FIG. 4 is called a triangular common path interferometer, in which a mirror M1 is placed at a position indicated by the broken line, beams divided by a beam splitter BS are again completely superimposed on each other by the beam splitter, and a spherical wave reaches the rear focal plane of the lens L. When the mirror M1 is placed at a position (indicated by the solid line) away by a from the broken line, the two beams are deviated in parallel and reach the surface of the detector D with an angle of $\theta$ shown in FIG. 4 to form an interference fringe. The apparatus shown in FIG. 5 uses a Michelson interferometer, in which mirrors of two light paths are respectively slightly inclined in a opposite direction (or only one of them) with respect to the optical axis. Then, an equivalent position M2' of a mirror M2 at the position of the mirror M1 produces an optical path difference $\theta x$ ($\theta$ is an angle formed between two beams) proportional to a distance x from the optical axis as compared with the mirror M1. Observing the mirror through a focusing lens 2, an interference fringe formed by the optical path difference between two beams is obtained at the surface of the detector D. FIG. 6 shows a square common path interferometer, in which light to be measured is divided into two beams by a beam splitter BS, and the beams are reversely turned around along the square light path and again joined together at the beam splitter BS to form an interference fringe on the detector D.

Preferably, a spatial interferogram detected by a two-dimensional photon counter as a detector D is divided into fine lengths in a direction (axis x) vertical to an interference fringe. The number of photons released into every divided fine length is integrated in a direction (axially) parallel to the interference fringe, where the length of division is determined so that the divided fine length and the total number of the integrated photons satisfy a certain relationship. The integrated total number of photons is subjected to a Fourier transform with the divided length as a unit. Generally, when the number of detected photons decreases, the S/N ratio decreases and the measuring accuracy is lowered. Accordingly, integration occurs in a direction (axis y) parallel to the interference fringe to increase the number of detected photons. The finer the division, the strength of the distribution of the interference fringes are faithfully detected but the total number of photons detected for one section decreases. If the division is rough, the total number of photons detected for one section increases, whereas if the division is excessively rough, the strength of the distribution of the interference fringes cannot be accurately grasped. Accordingly, the length of division is determined so that the divided fine length and the integrated total number of photons satisfy a certain relationship. For example, in order that the number of detected photons Ns for one section may be larger than the total number of noise Nn for section and be significant one, it is necessary for the number Ns to be larger than the unevenness of the number of detected photons Ns and the total number of noise Nn. The divided length of one section needs be determined so as to satisfy $$Ns \geq \sqrt{Ns + Nn}.$$

The spatial interferogram detected by the two-dimensional photon counter as the detector D, where ideal interference fringes are generated by the function of the optical system of the apparatus, may not be possible to be divided in the axis X, unlike the array element, but to be divided in consideration of the function of the optical system of the apparatus. That is, it is possible to correct the interference fringes at both ends of the spatial interference fringes.

Furthermore, various image processing can be made such as the spatial interferogram detected by the two-dimensional photon counter as the detector D is disassembled into spatial frequency components, and specific spatial frequency components are to cut flickering components corresponding to noise and unevenness.

The present invention was made to enable the Fourier spectroscopy of an extremely faint emission source not achieved by the prior art by using the two-dimensional photon counter capable of detecting photon receiving positions as the detector of a spatial interferogram type Fourier spectroscopic apparatus. Since this spectroscopic apparatus uses no movable parts, spectroscopy is not only easy but also since a filter or the like needs not be exchanged, spectroscopy can be made in a short period of time.

What is claimed is:

1. Fourier spectroscopic apparatus of a spatial interferogram type for extremely faint light comprising:
    a first optical system dividing an extremely faint light from a photon emitting source into two different light beams;
    a second optical system focusing interference fringes of the two different light beams; and
    a detector detecting focused interference fringes, the detector is a two-dimensional photon counter capable of detecting photon receiving positions.

2. An extremely faint light spectroscopic apparatus according to claim 1, wherein said first optical system and said second optical system comprise a double beam interferometer including a polarizer, a Wallaston prism, an analyzer and a focusing lens.

3. An extremely faint light spectroscopic apparatus according to claim 1, wherein said first optical system and said second optical system comprises a triangular common path interferometer.

4. An extremely faint light spectroscopic apparatus according to claim 1, wherein said first optical system and said second optical system comprise a Michelson interferometer.

5. An extremely faint light spectroscopic apparatus according to claim 1, wherein said first optical system and said second optical system comprise a square common path interferometer.

6. An extremely faint light spectroscopic apparatus according to claim 1, wherein said two-dimensional photon counter comprises a combination of a two-dimensional photon counting tube and a low persistence visicon.

7. An extremely faint light spectroscopic apparatus according to claim 1, wherein said two-dimensional photon counter is a photon counting type image measuring device.

8. An extremely faint light spectroscopic apparatus according to claim 1, wherein a spatial interferogram detected by said two-dimensional photon counter is divided into predetermined fine lengths in a direction vertical to an interference fringe thereof, a number of photons released into the divided fine lengths are integrated, the divided length is determined so that the divided fine length and the integrated total number of photons satisfy a predetermined relationship, and the total number of photons is subjected to Fourier transform with the divided length as a unit to obtain a spectra.

* * * * *

UNITED STATES PATENT AND TRADEMARK OFFICE
CERTIFICATE OF CORRECTION

PATENT NO. : 4,983,041

DATED : January 8, 1991

INVENTOR(S) : Fumio INABA et al

It is certified that error appears in the above-identified patent and that said Letters Patent is hereby corrected as shown below:

On the title page, Item [76], -- Tsutomu Ichimura, 301, No. 2 Greenheights Zuiho, 1-20, 1-chome, Mukaiyama, Sendai-shi, Miyagi-ken, Japan -- should be added.

Signed and Sealed this

Twenty-eighth Day of July, 1992

Attest:

DOUGLAS B. COMER

*Attesting Officer*     *Acting Commissioner of Patents and Trademarks*